United States Patent
Riff et al.

(10) Patent No.: US 6,889,119 B2
(45) Date of Patent: May 3, 2005

(54) ROBOTIC DEVICE FOR LOADING LABORATORY INSTRUMENTS

(75) Inventors: Michael Paul Riff, Burlington (CA); Thomas Ian Hatherley, Oakville (CA)

(73) Assignee: Thermo CRS, Ltd., Burlington (CA)

( * ) Notice: Subject to any disclaimer, the term of this patent is extended or adjusted under 35 U.S.C. 154(b) by 107 days.

(21) Appl. No.: 10/285,905

(22) Filed: Oct. 31, 2002

(65) Prior Publication Data

US 2003/0114961 A1 Jun. 19, 2003

Related U.S. Application Data

(60) Provisional application No. 60/330,832, filed on Oct. 31, 2001.

(51) Int. Cl.$^7$ ............................................. G06F 19/00
(52) U.S. Cl. ..................... 700/254; 700/254; 700/260; 700/261; 700/262; 901/14; 901/15; 901/16; 901/23; 901/41; 901/42; 414/696; 414/733; 414/751.1
(58) Field of Search ..................... 318/568.1, 568.11, 318/568.12, 568.2, 577; 319/212.61, 121.62, 121.63, 121.64, 121.82, 121.83; 700/259, 245, 254, 260, 261, 262; 414/696, 751.1, 733; 901/23, 14, 15, 16, 42, 41

(56) References Cited

U.S. PATENT DOCUMENTS

| | | | |
|---|---|---|---|
| 4,398,863 A | | 8/1983 | Shum |
| 4,682,805 A | | 7/1987 | Reynolds |
| 4,774,445 A | | 9/1988 | Penkar |
| 6,068,393 A | | 5/2000 | Hutchins |
| 6,070,109 A | * | 5/2000 | McGee et al. ............... 700/259 |
| 6,256,868 B1 | | 7/2001 | Sugito |
| 6,301,526 B1 | * | 10/2001 | Kim et al. ................... 700/260 |
| 6,321,137 B1 | * | 11/2001 | De Smet ..................... 700/245 |
| 6,334,078 B1 | * | 12/2001 | Matsui ........................ 700/245 |
| 6,408,224 B1 | * | 6/2002 | Okamoto et al. ............ 700/245 |
| 6,424,886 B1 | * | 7/2002 | Iversen et al. ............... 700/254 |
| 6,430,472 B1 | * | 8/2002 | Boillot et al. ................ 700/245 |
| 6,584,379 B1 | * | 6/2003 | Mukai et al. ................ 700/254 |
| 6,675,069 B2 | * | 1/2004 | Uratani ........................ 700/245 |
| 6,690,999 B2 | * | 2/2004 | Kimura ........................ 700/245 |

FOREIGN PATENT DOCUMENTS

| | | |
|---|---|---|
| EP | 0 728 559 B1 | 8/1996 |
| JP | 60131181 | 7/1985 |
| JP | 62201221 | 9/1987 |

OTHER PUBLICATIONS

Payandeh et al., A conttrol architecture for arm/hand manipulating system, 1991, IEEE, pp. 1440–1443.*
Suckau et al., Automation of MALDI–TOF analysis for proteomics, 1999, Internet, pp. 1–5.*
Cheng et al., Adaptive synchronization control of a robotic manipulator operating in an intelligent workcell, 1990, IEEE, pp. 119–126.*
Hoffman et al., Optimization of underfilling through software managemetn of process control, 1997, Internet, 1–11.*

* cited by examiner

Primary Examiner—Thomas G. Black
Assistant Examiner—McDieunel Marc
(74) Attorney, Agent, or Firm—Dorsey & Whitney LLP

(57) ABSTRACT

A robotic device for moving at least one object between locations, including a servo motor system having a single servo axis for effecting motion in at least two directions of motion. The robotic device includes a link arm rotationally coupled to said servo motor system for lifting and placing said at least one object, a head assembly having gripper arms for gripping and releasing said at least one object at said locations. The head assembly includes a leveling mechanism for maintaining said at least one object in a desired orientation, and a split ring sensing mechanism, disposed between said gripper arms, for determining the presence of said at least one object.

13 Claims, 6 Drawing Sheets

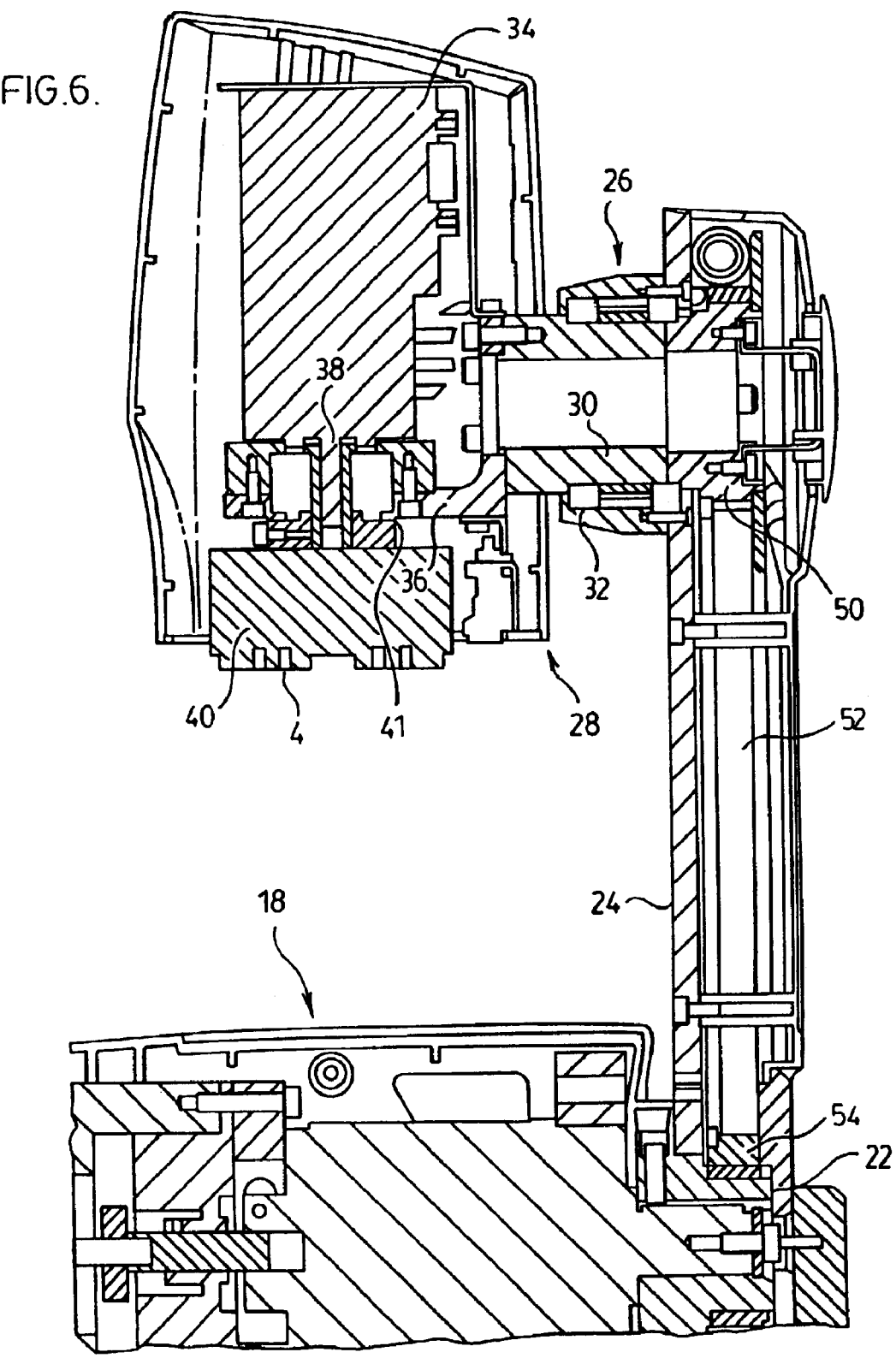

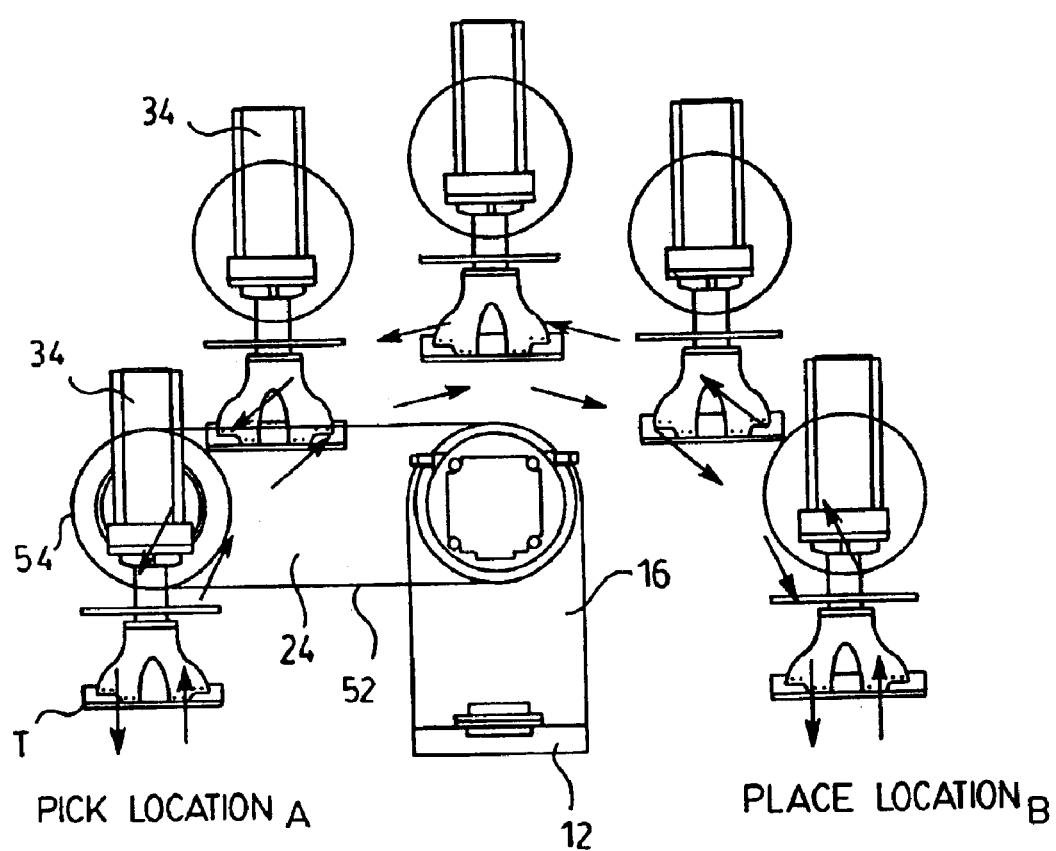

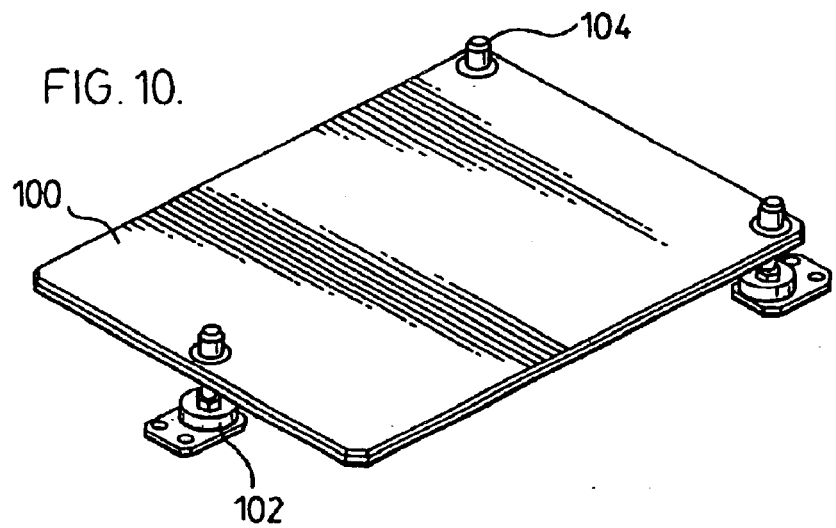
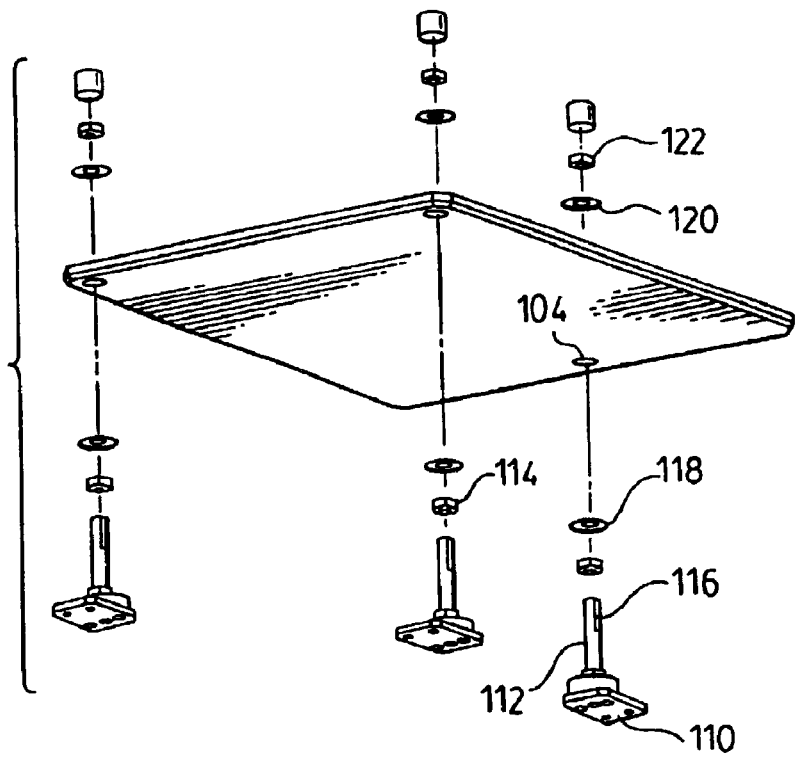

US 6,889,119 B2

ROBOTIC DEVICE FOR LOADING LABORATORY INSTRUMENTS

CROSS-REFERENCE TO RELATED APPLICATION

This application claims the benefit of U.S. application Ser. No. 60/330,832, filed Oct. 31/2001 which is hereby incorporated by reference as though fully set forth herein.

FIELD OF THE INVENTION

The present invention relates to a method and apparatus for the automated transfer of objects between locations.

BACKGROUND OF THE INVENTION

In medical, chemical and biological laboratories, microtiter plates are commonly used and are filled with various media. The media may either be in a liquid form, or in a more viscous form such as Agar. For efficient productivity of the laboratory, the use of a robotic device to move the microplates between locations is desirable. Such automated machines can produce considerably greater throughput than a technician. To this end there are several automated devices that are currently available to effect such transportation.

Traditionally, an articulated or cylindrical automated machine with three degrees of motion has been used. Such automated machines are often mounted on a substantially long linear axis and are moved through the entire system to load a plate from one instrument to another. Also, in more complicated systems, conveyors with escapements and slides are used as part of the system to move an object between spaced locations.

One of the disadvantages of these automated machines is that each requires a minimum of three axes of motion to transfer an object such as a microtiter plate. Typically, such machines require three to six motors to obtain the movement required at the various joints. During movement of an object between locations it is frequently necessary to maintain a fixed orientation for the object, such as maintaining a microtiter plate in a horizontal plane. On traditional machines, plate leveling is accomplished by means of a servomotor controlling an additional joint. This requires additional control functions and mechanical complexity.

In order to pass signals between the automated machine's motor and the controller, a flexible wire harness is often used, while another solution involves the use of conductive rings with metal brushes that slide along the rings to replace wire harnesses. A wire harness is susceptible to mechanical fatigue and failure, and takes a certain amount of space in the design. The drawbacks of using brushes and rings are that noise and sparks are generated by the brushes, and the mechanism requires regular maintenance. Typically, the above solutions involve substantially complex systems having a substantial number of parts requiring maintenance.

It is thus an object of this invention to obviate or mitigate at least one of the above mentioned drawbacks.

SUMMARY OF THE INVENTION

In one aspect, a robotic device comprises a base, an arm rotatable about a first axis relative to the base. A drive motor controls rotation of the arm about the first axis. A head is rotatably mounted on the arm for rotation about an axis parallel to the first axis, and a leveling mechanism operable between the base and the head assembly to maintain the head assembly in a predetermined orientation during rotation of the arm about the first axis.

BRIEF DESCRIPTION OF THE DRAWINGS

These and other features of the preferred embodiments of the invention will now be described by way of example only in the following detailed description in which reference is made to the appended drawings wherein.

FIG. 6 is a detailed sectional view on the line 6—6 of FIG. 5;

FIG. 7 is a schematic representation showing the movement of the robotic device between a pair of locations;

FIG. 10 is a perspective view of a station assembly used with the device shown in FIG. 1; and FIG. 11 is an exploded perspective view of the station shown in FIG. 10.

DESCRIPTION OF THE PREFERRED EMBODIMENTS

Figure 1:
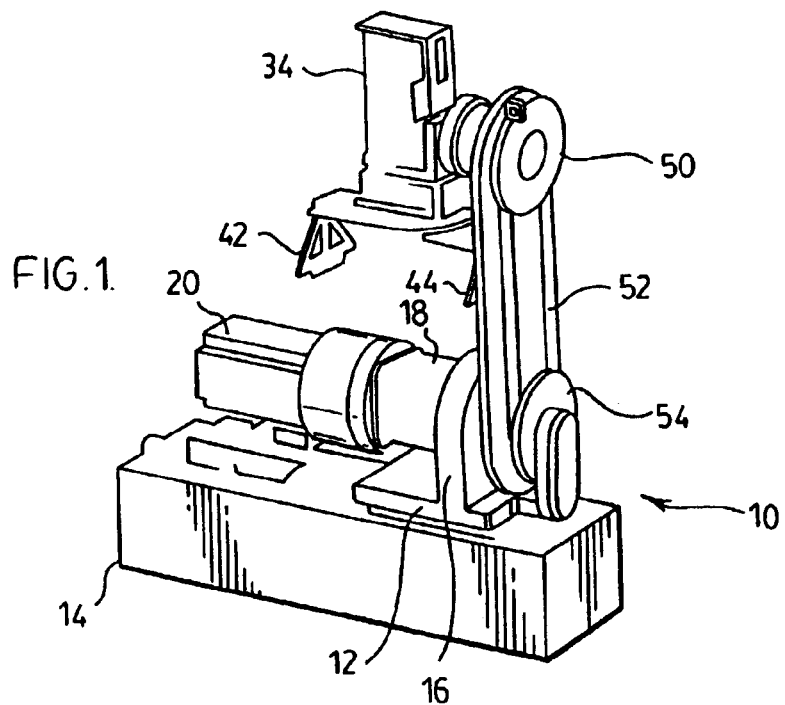
FIG. 1 is a perspective view of a robotic device.

Referring therefore to FIG. 1, a robotic device generally indicated 10 is secured through a base 12 to a workstation 14. The base 12 includes an upstanding flange 16 that carries a planetary gearbox 18. The gearbox supports a servo motor 20, which includes an encoder and associated circuitry to cause rotation of the armature of the motor 20 upon receipt of a control signal.

As can be seen in further detail in FIG. 6, the output from the motor 12 is transmitted through the gearbox 14 an output shaft 22. The shaft 22 is connected to a robot arm 24 that projects radially outwardly from the shaft 22. The arm 24 carries a bearing assembly 26 at the opposite end to the shaft 22 to support a head assembly 28. The head assembly 28 is supported on a tubular shaft 30 that is rotatable within bearing 32 and so is free to rotate relative to the arm 24. The head assembly 28 includes a base plate that supports a hand assembly 40. The hand assembly 40 is rotatably supported on the base plate 36 by a bearing 41 and a servo motor 34 is operable through a drive shaft 38 to rotate the hand assembly relative to the base plate 36. The bearing 41 is oriented to constrain rotation of the hand assembly about an axis orthogonal to the axis of rotation of the motor 12. The hand assembly 40 has a pair of fingers 42, 44 that can be moved toward or away from one another to engage or release an object. A sensor assembly 46 is incorporated into the hand assembly 40 to indicate the presence or absence of an object as will be described in further detail below. A servo A toothed pulley 50 is connected to the shaft 3 for rotation with the shaft and a drive belt 52 is entrained about the pulley 50. The belt 52 is also entrained about a lower toothed pulley 54 that is secured to a bracket 56 on the base 12. The lower toothed pulley 54 is secured so as to be stationary relative to the base 12 and is centered on the axis of rotation of the arm 24.

The circumferential position of the pulley 54 relative to the base may be adjusted by a clamp bolt 58 (FIG. 5) that is located within a slot 60 in the bracket 56 and so permits limited rotation of the lower pulley 54 relative to the base 12.

The limited adjustment available for the pulley 54 is transmitted through the belt 52 and causes a corresponding rotation of the shaft 30 and head assembly 28. This permits the orientation of the head assembly 28 to be adjusted into a preferred orientation relative to the base 12 that is maintained during the swinging movement of the arm 24.

Figure 5:
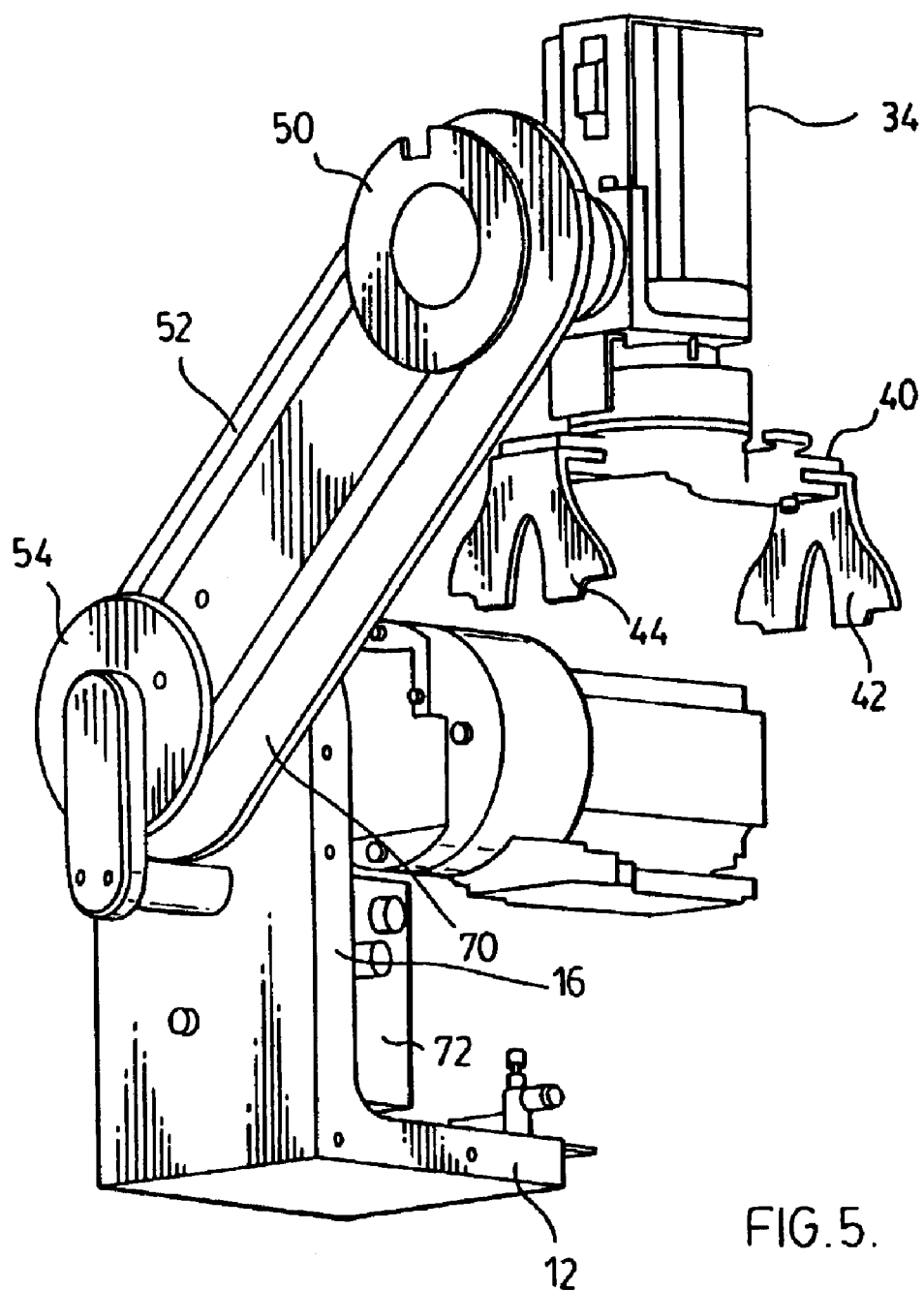
FIG. 5 is a perspective view similar to FIG. 1 with the device in an alternative configuration.

As may best be seen in FIG. 5, control signals and power to the motor 34 and hand assembly 40 is provided through a wiring harness 70 that passes through the centre of the tubular shaft 30 to the outer edge of the pulley 50. The harness 70 passes alongside the run of the belt 52 and through an aperture provided in the flange 16 adjacent to bracket 56 to a control box 72.

Figures 2, 3, 4:
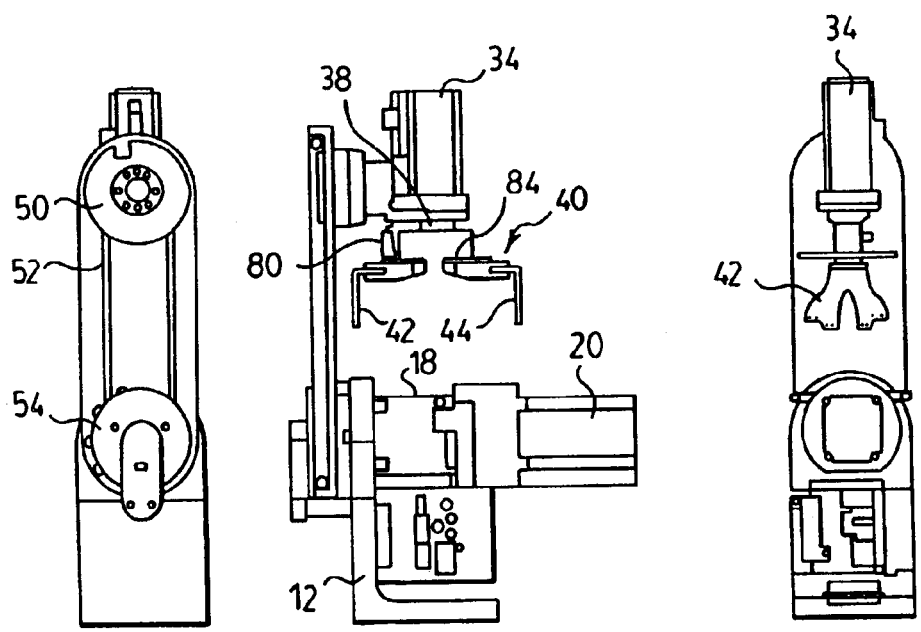
FIG. 2 is a front elevation of the device shown in FIG. 1.
FIG. 3 is a side elevation of the device shown in FIG. 1.
FIG. 4 is a rear elevation of the device shown in FIG. 1.

Referring again to FIGS. 1 and 3, the hand assembly 40 includes an actuator 80 to control sliding movement of the fingers 42, 44 toward and away from one another. The fingers 42, 44 have lower edges with apertures and pins 82 configured to engage standard formations on an object to be conveyed. The fingers 42, 44 are slideably mounted on a base plate 84 which in turn is rotatably supported on bearings 41 on the plate 36. Motor 34 is supported on the base plate 36 on a flexible coupling 88 formed by a double-sided tape such as that sold by 3M under the trademark VHB. The flexible coupling a high shear force to resist torque induced in the motor 34 through the output shaft 38 whilst allowing limited flexibility to accommodate alignment between the components in the head assembly 40.

Figures 8A, 8B, 8C:
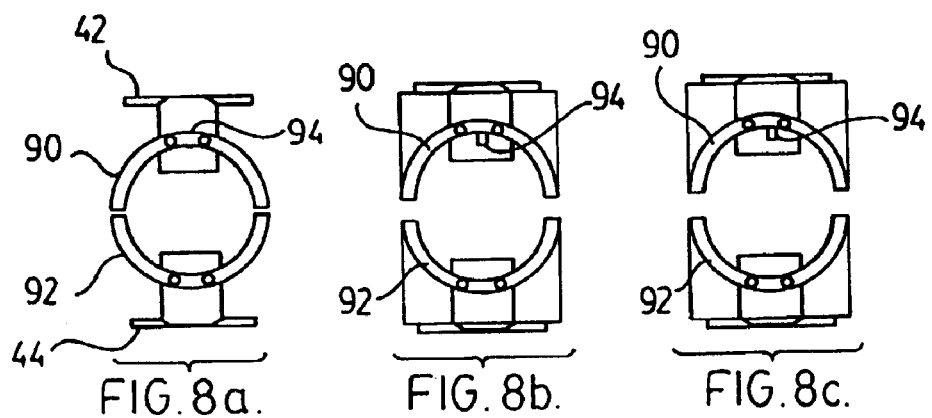
FIG. 8 is a set of figures showing a sensor mechanism used in conjunction with the device shown in FIG. 1.

The sensor assembly 46, shown in more detail in FIGS. 8 and 9, includes a pair of circular segments 90, 92, each secured a respective one of the fingers 42, 44. A proximity sensor 94 is carried on the base plate 36 and is typically an inductive sensor providing a signal indicating the presence or absence of a component. As may be seen in FIG. 8a, with the fingers 42, 44 moved together, the sensors are triggered indicating the presence of the ring 90 over the sensor 94. This indicates that the actuator has moved to the limit of its travel and no object has been located between the fingers 42, 44. In an alternative position shown in FIG. 8b, the fingers 42, 44 have been moved toward one another, but the sensor 94 remains uncovered, thereby not providing a control signal. The combination of a pressure signal from the actuator 80 and the lack of a sensor signal indicates that the hand is closed but not fully closed so as to be indicative of an object secured between the jaws.

In the third position shown in FIG. 8c, the sensor is uncovered but pressure is not applied to the actuator thereby indicating that the jaws are open.

Figures 9A, 9B, 9C:
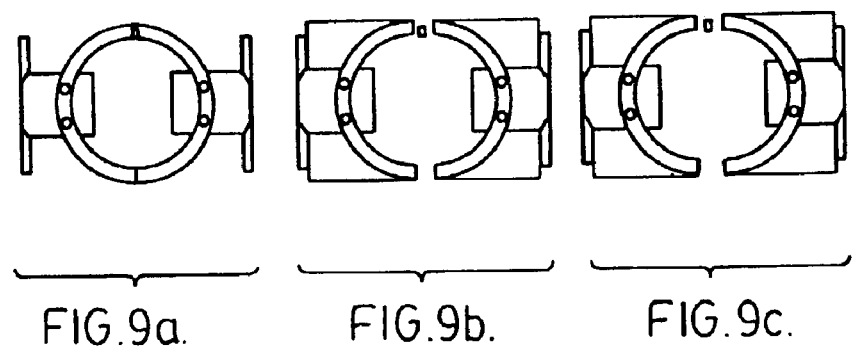
FIG. 9 is a view similar to FIG. 8, showing an alternative configuration of sensing mechanism.

The provision of the split ring formed by the two segments 90, 92 permits similar functionality to be achieved with the hand assembly 40 rotated through 90 degrees by the motor 34. Thus, as shown in FIG. 9a, with the fingers fully closed, the gap between the segments 90, 92 is closed causing the sensor to be triggered. In the orientation shown in FIG. 9b, the sensor is uncovered and no signal is received from the sensor.

In operation, the robot device 10 is located between a pick location indicated in FIG. 7 at A and a place location indicated in FIG. 7 at B. In the pick location the robot arm is operable to be positioned so that the jaws 42, 44 overlap the edges of a tray T and, through operation of the actuator 80 grip the sides of the tray T. The capture of the tray T between the fingers 40, 42 is signaled through the sensor corresponding to the condition shown in 8B. The control is then operable to rotate the motor 12 and cause the arm 24 to rotate about the axis of the motor. As the arm rotates, the belt 52 walks about the circumference of the pulley 54 and causes a corresponding rotation of the shaft 30 in the bearing assembly 26. The orientation of the head 28 is thus maintained as the arm rotates and thereby maintains the tray T in a horizontal disposition. Rotation continues until the tray T is moved to the place location B where the hand assembly may be released and the tray T deposited.

If during movement of the tray T from the pick location A to the place location B it is necessary to turn the tray T, the motor 34 may be operated to rotate it in a vertical axis and turn it through 90 degrees. During this movement the sensing ring moves from the position shown in FIG. 8b to that shown in FIG. 9b and maintains the logical control of the hand assembly on the tray.

To assist in accurate placement of the tray T at either the pick location or the place location, each of those locations may employ an adjustable platten that facilitates accurate placement of the tray T within a desired location. The platten is shown in FIGS. 10 and 11 and includes a support surface 100 supported on three support feet 102. Each of the support feet 102 is similar and includes a base 110 with a spindle 112 projecting upwardly from the base 110. The spindle 112 is threaded to receive a nut 114. The support surface 100 has an aperture 104 to receive each of the spindles 112 with clearance between the spindles 112 and the wall of the aperture 104. The spindle 112 is formed with flats 116 to receive a washer 118 that is formed with a corresponding slot. The washer 118 is thus unable to rotate on the spindle 112. A similar washer and nut 120, 122 is provided on the upper edge of the plate to secure the plate between the nuts 114, 122.

The nuts 114, 122 permit the height of the support surface 100 to be adjusted at each of the support feet 102 and the limited clearance between the spindle 112 and the aperture 104 permits lateral and longitudinal adjustment of the plate relative to the support feet. Accurate positioning of the surface 100 is thus possible, which can then be secured by tightening of the bolts 122. The flats 116 and the spindles 112 prevent rotation of the washers 118 and therefore prevent the transmission of a displacement due to rotation of the washers to the plate 100. The platten thus provides a method of accurate positioning beneath the tray to ensure that the tray is delivered to the correct location.

The arrangement of the stations A,B at either end of the arc of travel ensures that the placement of a tray or the surface 100 is performed in a substantially vertical manner. Thus, the tray T may be inserted within a rested support or well having vertical sides yet still be removed during initial movement of the arm.

It will also be noted that during movement of the arm 24 that the harness undergoes a minimal flexure over the range of movement of the arm. Thus stresses induced on the harness are minimized.

It will also be noted that the head assembly 28 is positioned over the gearbox 18 and motor 20 as the arm functions to move the tray between the locations. This, however, enables a very compact footprint to be obtained for the robot 10 without impeding the operation of the device.

It will be seen that a compact and simple device is provided that permits the movement of an object between spaced locations. The movement imposed on the object is smooth and continuous with a single acceleration and deceleration phase allowing for controlled movement of the object and its contents. The provision of the leveling mechanism provided by the belt and pulleys obviates the need for additional controls for a separate servo motor and consequently reduces the bulk of the device 10. It will be appreciated that if rotation of the hand assembly is not required the motor 34 may be omitted and the hand assembly secured directly to the base plate 36.

What is claimed is:

1. A robotic device comprising a base, an arm rotatable about a first axis relative to said base, a drive motor to control rotation of said arm about said first axis, a head assembly rotatably mounted on said arm for rotation about an axis parallel to said first axis, said head assembly includes a hand assembly to perimit gripping of an object to be moved, said hand assembly includes a sensor to determine the presence of an object to be moved, said sensor includes a pair of members, each associated with respective one of said fingers and each moveable with said finger between a first position in which a sensing element is active and a second position in which said sensing element is inactive, and a leveling mechanism operable between said base and said head assembly to maintain said head assembly in a predetermined orientation during rotation of said arm about said first axis.

2. A device according to claim 1 wherein said head assembly is rotatably mounted on said head assembly and a motor is mounted on said head assembly to control rotational movement of said hand assembly.

3. A device according to claim 2 wherein said hand assembly is rotatable about an axis orthogonal to said first axis.

4. A device according to claim 1 wherein said hand assembly includes a pair of fingers moveable toward or away from one another and said sensor determines the relative disposition of said fingers.

5. A device according to claim 1 wherein said hand assembly is rotatably mounted on said head assembly and a motor is mounted on said head assembly to control rotational movement of said hand assembly, and each of said pair of members is a part circular segment.

6. A robotic device comprising a base; an arm rotatable about a first axis relative to said base; a drive motor to control rotation of said arm about said first axis; a head assembly rotatably mounted on said arm for rotation about an axis parallel to said first axis, said head assembly includes a tubular shaft rotatably mounted on said arm; a leveling mechanism operable between said base and said head assembly to maintain said head assembly in a predetermined orientation during rotation of said arm about said first axis, said leveling mechanism includes a belt between said base and said head assembly, said belt entrained about a pair of pulleys, one of which is secured to said base and the other of which is secured to said head assembly, said one pulley is adjustable by rotation relative to said base and to cause a corresponding rotation relative to said arm and thereby cause a corresponding adjustment to said predetermined orientation, the other of said pulleys secured to said shaft; and a control harness, said control harness passes through said shaft and along said belt to said base.

7. A device according to claim 6 wherein said head assembly includes a hand assembly rotatably mounted on said head assembly and a motor is mounted on said head assembly to control rotational movement of said hand assembly.

8. A device according to claim 7 wherein a sensor is included in said hand assembly to determine the presence of an object to be moved.

9. A robotic system including a robotic device having a base, an arm rotatable about a first axis relative to said base, a drive motor to control rotation of said arm about said first axis, a head assembly rotatably mounted on said arm for rotation about an axis parallel to said first axis, and a leveling mechanism operable between said base and said head assembly to maintain said head assembly in a predetermined orientation during rotation of said arm about said first axis and a pair of stations to move an object between, at least one of said stations including a support surface with supports therefore to permit adjustment with six degrees of freedom.

10. A device according to claim 9 wherein said head assembly includes a hand assembly to permit gripping of an object to be moved.

11. A device according to claim 10 wherein said hand assembly is rotatably mounted on said head assembly and a motor is mounted on said head assembly to control rotational movement of said hand assembly.

12. A device according to claim 10 wherein a sensor is included in said hand assembly to determine the presence of an object to be moved.

13. A device according to claim 9 wherein said leveling mechanism includes an inextensible member between said base and said head assembly.

* * * * *